United States Patent [19]

Urben

[11] Patent Number: 4,711,967

[45] Date of Patent: Dec. 8, 1987

[54] PRODUCTION OF S-ARYL S-ALKYL DITHIOCARBONATES

[75] Inventor: Peter G. Urben, Kenilworth, United Kingdom

[73] Assignee: Courtaulds PLC, London, England

[21] Appl. No.: 856,505

[22] Filed: Apr. 28, 1986

[30] Foreign Application Priority Data

May 2, 1985 [GB] United Kingdom ................. 8511143

[51] Int. Cl.$^4$ ........................................... C07C 154/02
[52] U.S. Cl. .................................................... 558/243
[58] Field of Search ......................................... 558/243

[56] References Cited

FOREIGN PATENT DOCUMENTS 49-70926 7/1974 Japan ................................... 558/243

OTHER PUBLICATIONS

Rodd's Chemistry of Carbon Compounds, Supplement to Volume IIIA, Elsevier Scientific Publishing Company (1983), pp. 247-249.
Araki, Y., Bull. Chem. Soc. Japan, 1970, 43, pp. 252-257.

Primary Examiner—Henry R. Jiles
Assistant Examiner—Robert C. Whittenbaugh
Attorney, Agent, or Firm—Howson and Howson

[57] ABSTRACT

An S-aryl S-alkyl dithiocarbonate is prepared by pyroltically isomerizing an O-aryl S-alkyl dithiocarbonate at a temperature in the range 150°-600° C. The reaction product may be hydrolyzed to form an arenethiol or may be further reacted with an alcohol in the presence of a basic catalyst to form an aryl thioether.

9 Claims, No Drawings

PRODUCTION OF S-ARYL S-ALKYL DITHIOCARBONATES

This invention is concerned with the manufacture of S-aryl S-alkyl dithiocarbonates and with their use. One use of such materials is to hydrolyse them to arenethiols, which have several uses as chemical intermediates, so that this invention is also concerned with the manufacture of arenethiols. The S-aryl S-alkyl dithiocarbonates can also be used themselves as chemical intermediates in the preparation of certain agrochemicals and pharmaceuticals without proceeding via the arenethiol.

BACKGROUND OF THE INVENTION

The various methods of preparing an arenethiol from the corresponding phenol are described in Rodd's Chemistry of Carbon Compounds, Supplement to Volume III A (published by Elsevier in 1983), at pages 247 to 249. The recommended procedure is the Newman-Kwart rearrangement in which the phenol is reacted with a dialkyl thiocarbamoyl chloride, then heated and hydrolysed. A paper by Y. Araki in Bull. Chem. Soc. Japan 1970 43 pp 252–257 is reported; Araki describes the thermal rearrangement of O,S-diaryl dithiocarbonates to S,S-diaryl dithiocarbonates, which can be hydrolysed to form thiophenols. The O,S-diaryl dithiocarbonates are prepared by the reaction of a substituted phenol with an aryl chlorodithioformate. Japanese published unexamined patent application 49-70926 describes the rearrangement of O,S-diaryl dithiocarbonates to S,S-diaryl dithiocarbonates by catalysts which contain aluminium chloride in at least equal molar amounts in carbon disulphide.

An alternative known procedure is the Schonberg rearrangement:

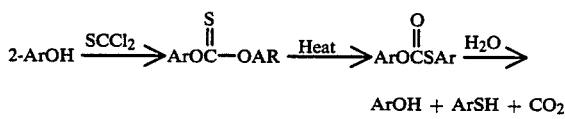

$$2\text{-ArOH} \xrightarrow{SCCl_2} \text{ArO}\overset{S}{\overset{\|}{C}}\text{-OAR} \xrightarrow{\text{Heat}} \text{ArO}\overset{O}{\overset{\|}{C}}\text{SAr} \xrightarrow{H_2O}$$

$$\text{ArOH} + \text{ArSH} + CO_2$$

(where Ar represents an aryl group)
This procedure has the disadvantages that only half the phenol used can be converted to arenethiol (yields are much lower in practice), the noxious chemical thiophosgene is required and the separation of equal amounts of arenethiol and phenol is difficult. The corresponding O-aryl O-alkyl thiocarbonates do not rearrange when heated; they lose carbonyl sulphide to form an aryl alkyl ether. Similarly S-aryl O-alkyl dithiocarbonates lose carbonyl sulphide on heating, forming an aryl alkyl thioether.

SUMMARY OF THE INVENTION

We have found that O-aryl S-alkyl dithiocarbonates, surprisingly, do not lose carbonyl sulphide on heating but isomerise to S-aryl S-alkyl dithiocarbonates in high yield.

A process according to the present invention for the preparation of an S-aryl S-alkyl dithiocarbonate comprises pyrolytically isomerising an O-aryl S-alkyl dithiocarbonate at a temperature in the range from 150° to 600° C.

The resulting S-aryl S-alkyl dithiocarbonates can be hydrolysed according to the invention in the presence of a base to form an arenethiol and can be further reacted with an alcohol in the presence of a basic catalyst to form an aryl thioether.

DESCRIPTION OF PREFERRED EMBODIMENTS

A temperature in the range from 200° C. to 300° C. is preferred for the pyrolysis, particularly from 250° to 280° C. The time of reaction can for example be from 0.5 to 10 hours. Flash pyrolysis, that is, in the vapour phase, at higher temperatures, for example above 300° C. up to 600° C., is an alternative preferred procedure.

The aryl radical is preferably a phenyl or naphthyl radical, a mono- or di-alkyl- or -halo-substituted phenyl radical or a phenyl radical substituted by an alkylthiocarbonyl thio group. The alkyl substituents and the S-alkyl radical of the dithiocarbonate desirably contain 1 to 6 and preferably 1 to 4 carbon atoms and are more especially methyl and ethyl.

A convenient total synthesis of the S-aryl S-alkyl dithiocarbonate from easily available starting materials comprises reacting a phenolate with carbon disulphide to form a xanthate, reacting the xanthate with an alkylating reagent to form the O-aryl S-alkyl dithiocarbonate (alkyl xanthate) and then pyrolysing the product to form the isomeric S-aryl S-alkyl dithiocarbonate. This can be hydrolysed to form an arenethiol if desired.

The process of the present invention prepares the S-aryl S-alkyl dithiocarbonate and arenethiol in at least as high a yield as the Newman-Kwart rearrangement; for example 90 percent conversion of xanthate to arenethiol can be achieved. The reagents required, viz. carbon disulphide and an alkylating agent, are more readily available than the dialkyl thiocarbamoyl chloride required in the Newman-Kwart rearrangement.

The total synthesis referred to above is illustrated in the following scheme using a mononuclear phenol (polynuclear phenols, such as naphthol, are embraced in the term "phenol"):

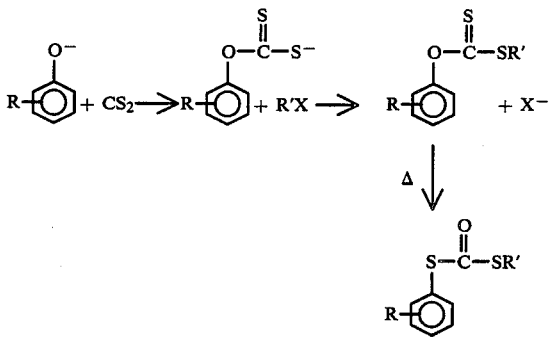

where R is hydrogen or an organic or inorganic radical stable to the reactants and the reaction conditions, R' is alkyl, R'X is an alkylating agent (for example an alkyl chloride, an alkyl bromide, an alkyl sulphate, or an alkyl sulphonate) and Δ signifies heat input necessary to the pyrolysis. The pyrolysis is preferably carried out in the absence of solvent.

Examples of phenols which can be converted to the corresponding S-aryl S-alkyl dithiocarbonate include phenol itself, o-, m- and p-cresol which can be converted to an S-cresyl S-alkyl dithiocarbonate via the O-cresyl S-alkyl dithiocarbonate; and dialkylphenols such as 2,6- or 3,5-dimethylphenol which can be converted to an S-dimethylphenyl S-alkyl dithiocarbonate via the O-dimethylphenyl S-alkyl dithiocarbonate. Some of the methyl- and dimethyl-substituted thiophenols which can thereby be prepared by hydrolysis, particularly 4-methylthiophenol, have a commercial market, as has thiophenol itself which is an intermediate for the production of edifenphos, a pesticide for use on rice.

The scheme may be continued for the preparation of arenethiols as follows:

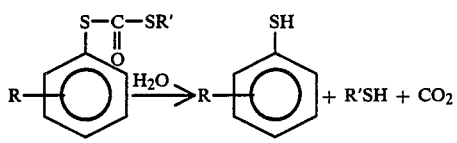

The hydrolysis is preferably carried out in the presence of a base, for example an alkali such as sodium hydroxide or potassium hydroxide or aqueous ammonia or an organic nitrogen base such as an amine, pyridine or imidazole.

When preparing the arenethiol the hydrolysis is preferably carried out without isolating the S-aryl S-alkyl dithiocarbonate from the pyrolysis reaction product. The small proportion of by-products contained therein include compounds which can themselves be hydrolysed to an arenethiol.

It will be noted that the manufacture of arenethiol is accompanied by the production of a mercaptan (R'SH) and such materials are also articles of commerce. The nature of R' in the alkylating agent (R'X) may be varied to produce mercaptans of choice or to realise the easy separation of the arenethiol and mercaptan by distillation; the use of a methyl group as R' is preferred for the latter purpose.

Alternatively the S-aryl S-alkyl dithiocarbonate can be reacted with a dialkylamine to give the arenethiol, alkyl mercaptan and a tetraalkyl urea, which may be commercially useful as a solvent or catalyst.

The phenol starting material may be a polyhydroxyarene, with each hydroxyl group eventually substituted by the group

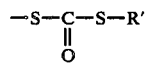

by the process of this invention. The yields of the SS'-arylene di(S-alkyl dithiocarbonate) from dihydroxybenzenes decrease in the order resorcinol, p-hydroxyphenol and catechol. These derivatives may be hydrolysed to the corresponding arenedithiols.

The S-aryl S-alkyl dithiocarbonate can alternatively be reacted with an alcohol in the presence of a basic catalyst to form an aryl thioether. It can for example be reacted with methanol to produce thioanisole or with ethylene glycol to produce phenylmercaptoethanol, both of which are used in the manufacture of agricultural chemicals and pharmaceuticals, e.g. sulindac from thioanisole and sulfinpyrazone from phenylmercaptoethanol, or with allyl alcohol to produce phenyl allyl sulphide which is used in formation of the B/C ring in total steroid synthesis, e.g. the manufacture of oestrogen. The reaction is preferably carried out at a temperature in the range from 50° to 200° C. In many cases it may conveniently be at the reflux temperature of the alcohol. Examples of basic catalysts which can be used are the alkali metal alcoholate of the alcohol to be reacted, alkali metal hydrides or an organic nitrogen base.

The invention is illustrated by the following Examples in which parts are by weight.

EXAMPLE 1

5 parts of O-phenyl S-methyl dithiocarbonate were heated at 200° C. for 30 minutes and a sample submitted to infra-red spectrum analysis which showed the appearance of C=O signals in addition to C=S signals. The temperature was raised to 250° C. over a three hour period and then the reaction mass was allowed to cool. The spectrum analysis of a sample showed that the C=S signals had almost disappeared. Gas chromatography demonstrated that there was little starting material and a predominant product of boiling point similar to that of the starting material. The reaction mass had darkened during the pyrolysis, but at no time had there been any significant evolution of gas or vapour.

No attempt was made to separate the S-aryl S-alkyl dithiocarbonate from the reaction mass. Instead a solution of 5 parts of NaOH in wet methanol was introduced into the reactor. The reaction mass dissolved with an exothermic reaction in the NaOH solution and a white precipitate appeared. The liquor was acidified and toluene added to partition the product. Gas chromatography showed that the toluene layer contained only two significant components boiling higher than toluene—benzenethiol and phenol—and these were present in a weight ratio of 4:1.

EXAMPLE 2

500 g liquid O-m-cresyl S-methyl dithiocarbonate was heated to 280° C. The resultant exotherm was controlled by addition of more of the same material, until a total of 1.5 kg was in the flask (which took 30 min). The mixture was then held at 280° C. for 1 hour.

The material was allowed to cool. Gas chromatography (g.c) indicated 0.1 percent starting material (originally—99 percent by g.c.), 89 percent S-m-cresyl S-methyl dithiocarbonate of slightly higher boiling point and thiocresol, cresyl disulphide, cresyl methyl disulphide and dicresyl dithiocarbonate as by-products. Infra-red showed that the prominent C=S absorptions in the starting material had vanished, and C=O signals had appeared.

A second similar experiment was performed and the products combined. Of this, 2222 g was hydrolysed by 13.5 moles 40 percent aqueous sodium hydroxide solution, at 100° C. for 5 hours. The organic layer of the product was crude m-thiocresol. The 1487 g crude m-thiocresol was distilled at 0.1 atm. pressure, b.p. 116°–120° C. to give 1145 g substantially pure m-thiocresol. There was also a forerun of 55 g (above 90 percent thiocresol). The pot residue (250 g) contained thiocresol, cresyl disulphide and S-cresyl S-methyl dithiocarbonate in roughly equal proportions.

EXAMPLES 3 TO 7

Using the procedure of Example 2, the following methyl xanthates (O-aryl S-methyl dithiocarbonates) set out in Table 1 were converted to S-aryl S-methyl dithiocarbonates. A total of 1.5 kg of the methyl xanthate was pyrolysed in each case. Some of the methyl xanthates are solids at room temperature; in these cases they were added as liquids at a temperature just above their melting point.

TABLE

| Example | Starting material | Melting point | Product |
|---|---|---|---|
| 3 | O—phenyl S—methyl dithiocarbonate | Liquid at room temp. | S—phenyl S—methyl dithiocarbonate |
| 4 | O—o-cresyl S—methyl dithiocarbonate | 28° C. | S—o-cresyl S—methyl dithiocarbonate |
| 5 | O—p-cresyl S—methyl dithiocarbonate | 26° C. | S—p-cresyl S—methyl dithiocarbonate |
| 6 | O—2,6-dimethylphenyl S—methyl dithiocarbonate | 35° C. | S—2,6-dimethyl-phenyl S—methyl dithiocarbonate |
| 7 | O—3,5-dimethylphenyl S—methyl dithiocarbonate | 55° C. | S—3,5-dimethylphenyl S—methyl dithiocarbonate |
| 8 | O—p-isopropylphenyl S—methyl dithiocarbonate | Liquid at room temp. | S—p-isopropylphenyl S—methyl dithiocarbonate |

In each case the S-aryl S-methyl dithiocarbonate was produced in about 90 percent yield.

The product of each Example was hydrolysed using 9 moles 40 percent aqueous sodium hydroxide at 100° C. for 5 hours and was purified as described in Example 2. The results obtained were as follows:

Example 3—substantially pure thiophenol produced in 90 percent yield. The main impurity was phenyl disulphide.

Examples 4 and 5—substantially pure o-thiocresol and p-thiocresol respectively produced in above 90 percent yield.

Examples 6 and 7—substantially pure 2,6-dimethylthiophenol and 3,5-dimethylthiophenol respectively produced in 80 percent yield. The main impurity was the S-aryl S-methyl dithiocarbonate (i.e. incomplete conversion under these reaction conditions).

Example 8—substantially pure p-isopropylthiophenol produced in above 90 percent yield.

EXAMPLE 9

A sample of crude O-2,6-dimethyl-phenyl S-butyl dithiocarbonate was prepared (about 98 percent pure by g.c).

This was heated to 260°–290° C. for one hour. The product showed virtually no C=S signals in the infrared spectrum and did show C=O signals at 1650 and 1730 cm$^{-1}$. g.c. showed it to be 94 percent of a single component, of slightly longer retention time than the starting material (of which 0.8 percent remained). This product was S-2,6-dimethylphenyl S-butyl dithiocarbonate.

EXAMPLE 10

A sample of distilled O-p-chlorophenyl S-methyl dithiocarbonate was heated to 250°–260° C. for 3 hours. The product was 82 percent of an S,S-dithiocarbonate having C=O signals and no C=S signals in the infrared spectrum. This was S-p-chlorophenyl S-methyl dithiocarbonate.

EXAMPLE 11

A sample of O-p-fluorophenyl S-methyl dithiocarbonate was heated for 2 hours at 260°–270° C. The product contained S-p-fluorophenyl S-methyl dithiocarbonate and the starting material in the ratio of 95:5.

EXAMPLE 12

Preparation of Phenylmercaptoethanol

S-phenyl S-methyl dithiocarbonate prepared as described in Example 3 (5 g), ethylene glycol (5 ml), and imidazole (0.1 g) were placed in a stirred flask and heated to 160° C. for 10 hours. At this time, the major component (excepting ethylene glycol) was identified by g.c. comparison with an authentic sample as phenylmercaptoethanol (g.c. suggested over 90 percent yield).

EXAMPLE 13

Preparation of Thioanisole

S-phenyl S-methyl dithiocarbonate (5 g) was mixed with methanol (5 g) in which sodium (50 mg) had been dissolved. The mixture was heated to reflux for eight hours. The mixture was then mixed with water, and the water-immiscible layer analysed by g.c. It was above 90 percent thioanisole (by comparison with an authentic sample).

EXAMPLE 14

S-phenyl S-methyl dithiocarbonate (5 g) was mixed with allyl alcohol (10 ml) to which sodium hydride (30 mg) had been added. The mixture was heated to reflux for 12 hours. Work-up was by addition to water, separation and washing the organic phase with more water. g.c. assay indicated 95 percent of one component whose N.m.r. and infra-red spectrum were consistent with phenyl allyl sulphide.

I claim:

1. A process for the preparation of an S-aryl S-alkyl dithiocarbonate of the formula

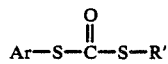

where Ar is a phenyl or naphthyl group which may be substituted, and R' is an alkyl group, wherein an O-aryl S-alkyl dithiocarbonate of the formula

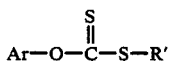

where Ar and R' are as previously stated is pyrolytically isomerised at a temperature in the range from 200° to 600° C. to produce said S-aryl S-alkyl dithiocarbonate.

2. A process according to claim 1, wherein the pyrolysis is carried out at a temperature in the range from 200° to 300° C.

3. A process according to claim 1, wherein the pyrolysis is carried out at a temperature in the range from 250° to 280° C.

4. A process according to claim 1, wherein the pyrolysis is carried out in the vapour phase at a temperature above 300° C. up to 600° C.

5. A process according to claim 1 wherein the aryl radical of the O-aryl S-alkyl dithiocarbonate is selected from the group consisting of unsubstituted phenyl and naphthyl and phenyl substituted by one or two alkyl or halo substituents or an alkyl thiocarbonylthio group and each alkyl group in the O-aryl S-alkyl dithiocarbonate is of 1 to 4 carbon atoms.

6. A process according to claim 1, wherein the O-aryl S-alkyl dithiocarbonate has been obtained from a phenolic compound selected from phenol, o-, m- and p-cresol, 2,6- and 3,5-dimethylphenol, resorcinol, p-isopropylphenol p-fluorophenol and p-chlorophenol.

7. A process according to claim 1, wherein O-phenyl S-methyl dithiocarbonate is pyrolytically isomerised to S-phenyl S-methyl dithiocarbonate.

8. A process according to claim 1, wherein an O-cresyl S-methyl dithiocarbonate is pyrolytically isomerised to the corresponding S-cresyl S-methyl dithiocarbonate.

9. A process according to claim 1, wherein an O-dimethylphenyl S-($C_1$–$C_4$-alkyl) dithiocarbonate is pyrolytically isomerised to the corresponding S-dimethylphenyl S-alkyl dithiocarbonate.

* * * * *